United States Patent [19]

Coutré et al.

[11] Patent Number: 5,643,212

[45] Date of Patent: Jul. 1, 1997

[54] INFUSION PUMP MANAGEMENT SYSTEM FOR SUGGESTING AN ADAPTED COURSE OF THERAPY

[76] Inventors: James E. Coutré, 114 Stone Root La., Concord, Mass. 01742; Wayne P. Griffin, 55 Surrey La., Dracut, Mass. 01826; Charles M. Crisler, 10 Sunridge Rd., Windham, N.H. 03087

[21] Appl. No.: 207,574

[22] Filed: Mar. 7, 1994

Related U.S. Application Data

[62] Division of Ser. No. 882,692, May 12, 1992, Pat. No. 5,317,506, which is a division of Ser. No. 304,068, Jan. 30, 1989, Pat. No. 5,153,827.

[51] Int. Cl.$^6$ .............................. A61M 5/14; G06F 19/00
[52] U.S. Cl. ..................... 604/131; 128/DIG. 12; 128/DIG. 13
[58] Field of Search .............. 364/413.02, 413.01; 604/66, 65, 67, 246, 1.31; 128/DIG. 12, DIG. 13

[56] References Cited

U.S. PATENT DOCUMENTS

| | | | |
|---|---|---|---|
| 4,032,908 | 6/1977 | Rice et al. | 340/213 R |
| 4,126,132 | 11/1978 | Portner et al. | 128/214 F |
| 4,373,527 | 2/1983 | Fischell | 128/260 |
| 4,464,172 | 8/1984 | Lichtenstein | 604/65 |
| 4,526,404 | 7/1985 | Vasquez | 283/79 |
| 4,538,138 | 8/1985 | Harvey et al. | 340/521 |
| 4,553,958 | 11/1985 | LeCocq | 604/67 |
| 4,573,994 | 3/1986 | Fischell et al. | 604/891 |
| 4,619,653 | 10/1986 | Fischell | 604/891 |
| 4,696,671 | 9/1987 | Epstein et al. | 604/67 |
| 4,705,506 | 11/1987 | Archibald | 604/81 |
| 4,730,849 | 3/1988 | Siegel | 283/70 |
| 4,731,051 | 3/1988 | Fischell | 604/67 |
| 4,732,411 | 3/1988 | Siegel | 283/75 |
| 4,756,706 | 7/1988 | Kerns et al. | 604/66 |
| 4,778,449 | 10/1988 | Ucher et al. | 604/65 |
| 4,784,645 | 11/1988 | Fischell | 604/153 |
| 4,811,844 | 3/1989 | Moulding Jr. et al. | 206/459 |
| 4,816,208 | 3/1989 | Woods et al. | 376/259 |
| 4,817,044 | 3/1989 | Ogren | 364/550 |

(List continued on next page.)

OTHER PUBLICATIONS

Morell, J., et al., "Receptivity of Physicians in a Teaching Hospital to a Computerized Drug Interaction Monitoring and Reporting System", Med. Care, 15, No. 1, pp. 68–78 (Jan. 1977).

Kenyon, N.C., et al., "A Microcomputer System for the Identification of Drug Interactions," J. Med. Eng. & Tech., vol. 7, No. 5 (Sep. Oct. 1983), pp. 243–246.

Hokanson, J.A., et al., "The Feasibility of Barcode–Based Dispensing Quality Assurance Programs," Drug Intell. & Clin. Pharm. 18, pp. 76–78 (Jan. 1984).

Rappoport, A.E., "A Hospital Patient & Laboratory Machine–Readable Identification System (MRIS) Revisited," J. Med. Syst. 8 (1–2) pp. 133–156 (Apr. 1984).

Nold, E.G., and Williams, T.C., "Bar Codes and Their Potential Applications in Hospital Pharmacy," Am. J. Hosp. Pharm. 42 (12) pp. 2722–2732 (Dec., 1985).

Kirking, D.M., et al., "Detecting and Preventing Adverse Drug Interactions: The Potential Contribution of Computers in Pharmacies," Soc. Sci. Med., vol. 22, No. 1, pp. 1–8 (1986).

Craig, J.A., and Eves, G.B., "Minimizing Drug Misuse Among Elders: A Proposal," Public Health Rep. 102(1), pp. 86–90 (Jan.–Feb., 1987).

*Primary Examiner*—Robert A. Weinhardt
*Assistant Examiner*—Felicia Ives
*Attorney, Agent, or Firm*—Neal D. Marcus; Brian R. Woodworth

[57] ABSTRACT

A system of infusing fluids in a patient includes an infusion pump for infusing fluids into a patient in accordance with instructions to carry out a desired course of infusion therapy. The system includes a physiological sensor for sensing conditions of the patient during the course of the infusion and a remote infusion controlling system for monitoring the course of the infusion and generating suggested adapted instructions.

11 Claims, 14 Drawing Sheets

U.S. PATENT DOCUMENTS

| | | | |
|---|---|---|---|
| 4,828,545 | 5/1989 | Epstein et al. | 604/66 |
| 4,835,372 | 5/1989 | Gombrich et al. | 235/375 |
| 4,839,806 | 6/1989 | Goldfischer et al. | 364/413.02 |
| 4,847,764 | 7/1989 | Halvorson | 364/413.02 |
| 4,853,521 | 8/1989 | Clacys et al. | 235/375 |
| 4,857,713 | 8/1989 | Brown | 735/375 |
| 4,857,716 | 8/1989 | Gombrich et al. | 235/462 |
| 4,865,584 | 9/1989 | Epstein et al. | 604/67 |
| 4,871,351 | 10/1989 | Feingold | 604/66 |
| 4,898,578 | 2/1990 | Rubalcaba, Jr. | 604/66 |
| 4,919,596 | 4/1990 | Slate et al. | 417/18 |
| 4,925,444 | 5/1990 | Orkin et al. | 604/80 |
| 4,951,029 | 8/1990 | Severson | 340/506 |
| 5,019,974 | 5/1991 | Beckers | 364/413.02 |
| 5,041,086 | 8/1991 | Koenig et al. | 605/65 |
| 5,072,383 | 12/1991 | Brimme et al. | 364/413.02 |
| 5,088,981 | 2/1992 | Howson et al. | 604/31 |
| 5,100,380 | 3/1992 | Epstein et al. | 604/67 |
| 5,108,367 | 4/1992 | Epstein et al. | 604/67 |

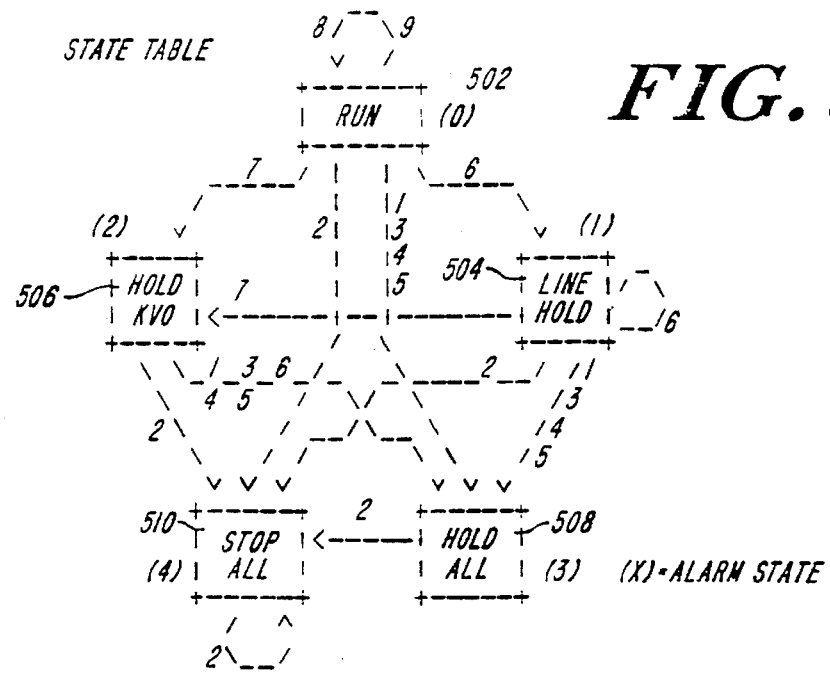

FIG. 35

| ALARM PRIORITY TABLE | | |
|---|---|---|
| PRIORITY | ALARM DESCRIPTION | PUMP SIGNAL SOURCE |
| 1 | CASSETTE UNLOCKED | INTERLOCK SWITCH |
| 2 | PUMP FAILURE | |
| 3 | OCCLUSION IN PATIENT (OUTPUT) LINE | PRESSURE DETECTOR ALGORITHM |
| 4 | COLLECTION CONTAINER FULL | CONTAINER SENSOR |
| 5 | AIR OR OCCLUSION IN PRIMARY INPUT LINE | PRESSURE DETECTOR ALGORITHM |
| 6 | AIR OR OCCLUSION IN SECONDARY INPUT LINE | PRESSURE DETECTOR ALGORITHM |
| 7 | PROGRAMMED RATE TOO FAST | |
| 8 | EMPTY CONTAINER ON INPUT LINE | |
| 9 | CALLBACK REQUESTED | ENTRY OF INTERMITTENT |

FIG. 36

INFUSION PUMP MANAGEMENT SYSTEM FOR SUGGESTING AN ADAPTED COURSE OF THERAPY

This application is a division of application Ser. No. 07/882,692, filed May 12, 1992, now U.S. Pat. No. 5,317,506, which is a division of application Ser. No. 07/304,068, filed Jan. 30, 1989, now U.S. Pat. No. 5,153,827.

FIELD OF THE INVENTION

This invention relates to systems for infusing fluids into a patient and more particularly to systems for managing and analysis of prescribed infusion programs.

BACKGROUND

Intravenous infusion therapy is often necessary to administer medications or other fluids directly into the circulatory system of a patient. Epstein, et al., U.S. Pat. No. 4,696,671, assigned to the current assignee and incorporated herein by reference, discloses an infusion pumping system capable of administering multiple infusates at individually programmable rates, volumes, and sequences. This system uses one or more single pump systems each of which pumps all plural fluids through one or more fluid input ports and one outlet port. This pump system increases the ability to administer complex programs of infusion therapies and reduces the time and labor required by nurses or other health practitioners in setting up and monitoring infusions while improving the reliability of proper infusion.

One or more infusions to be administered to a patient are prescribed by the patient's physician. A pharmacy, generally located within the patient's hospital or clinic, makes up the infusion according to the physician's prescription. The pharmacist places the infusion solution in a bag, bottle, syringe, or other container and labels the container. The label contains data to identify the patient, physician, medications prescribed, and a control number. The label is generally typed or printed in human readable characters only. The container is transported to the patient's location. A nurse or other health practitioner hangs the container from a rack. The nurse runs a tube from the container to the infusion pumping system, such as that disclosed by Epstein, et al. for pumping or gravity feeding the infusion solution to the patient. The nurse then enters all data regarding the infusion program manually, generally through a keyboard, into the pumping system. The data includes, for example, the rate of infusion, the total volume to be infused, and which of the plural lines the infusion is to use.

Hospitals maintain a large inventory of drugs that are kept up to date in volume and availability and size scaling. In addition, each hospital may develop its own vocabulary of drug identification and relies on pharmacist expertise to prevent incompatible drug administration. Manual treatment of this type of infusion system data is disadvantageous because it is labor and time consuming and the possibility for incorrect data treatment is greater.

SUMMARY OF THE INVENTION

The infusion system of the present invention contemplates a system for managing the infusion of one or more drug formulations to a patient from the make up of the infusion in the pharmacy to the generation of a report for hospital records and analysis after the infusion is complete.

The infusion management system of the present invention provides a computer-based pharmacy management system, located in a hospital or clinic's pharmacy, remote from the infusion pumping system. All prescriptions for intravenous infusions are entered into the system when the pharmacist makes up the prescribed formulation. The system prompts the pharmacist or other user for the necessary patient identification data and prescription data, such as the drug to be infused, the carrier solution if any, the concentration of the drug in the carrier solution, and the infusion regimen (continuous, maintenance, or intermittent and rate, volume and infusion frequency). The data entered can be subsequently edited. After all data has been correctly entered, the system makes a bar code readable label which is applied to the outside of the container in which the infusion solution is placed.

The pharmacy management system also includes a drug database which stores drugs by name, mnemonic, and I.D. number. The database also includes a matrix of drug incompatibility. If two incompatible drugs are to be mixed in a single solution, the system alerts the user.

The management system also produces reports to be included on the patient's record or chart. Further, the management system tracks the inventory of drugs by monitoring the precise amount of drugs used and the nature of this drug source. This data may be transferred to the hospital's existing drug inventory control system for more accurate monitoring and ordering of drugs.

The labeled container containing the infusion formulation is transferred to the patient by usual methods either within the hospital or to the patient's home in the case of remote infusion control. The user, a nurse or other health practitioner, using a bar code reader associated with each pump system, enters the data from the formulation container label into the infusion pumping system where it is displayed and accepted. The pumps serial port may be used for this purpose. Data can also be entered manually in addition to or in lieu of entry by bar code reader. The pumping system prompts the user for any necessary data that is missing from the read label but required by the pumping system before the infusion program can begin. To accommodate emergency situations, the pumping system allows an overrider. After entering the data on the solution container, the user completes the infusion programming by entering the start time. A delayed start time provides flexibility in administration. Preprogramming of functions is useful when the user is expecting a patient to arrive from, for example, an operating room and wants to get the infusion up in advance. Alternatively, an advance set-up reduces the risk of error due to setting up an infusion too quickly and allows the patient to be connected to the infusion system more rapidly upon arrival.

The infusion pumping system has several input lines for infusing more than one formulation. A similar procedure is used to program each line on the pumping system and the pump itself can identify inappropriately scheduled drugs.

The infusion pumping system performs several checks to ensure the data is correct. It verifies that the patient identification is correct and that the patient is not allergic to any of the medications in the solutions and allows the user to confirm that all data is correct. The user can override the data on the bar code label by manually entering different data.

The infusion pumping system of the present invention also contemplates an improved alarm handler system. During operation, the pumping system can generate a variety of alarm conditions of varying severity. Some alarm conditions, such as various pump failures, unlocked cassette, and patient line occlusion require stopping all pumping immediately. Other alarms, such as air in a secondary input line merely require temporarily holding the pumping on that line until the alarm condition has been cleared while other lines continue to infuse. Finally, alarms such as an empty bottle on one of the input lines do not effect pumping at all. Also, several alarms can exist simultaneously if, for example, a second alarm occurs before a first alarm has been cleared.

The present invention provides an alarm handler capable of dealing with many alarms at once. The alarm handler ranks the alarms by degree of urgency. The alarms are stored in a stack with the most urgent presented to the user for clearing first. Alarms of the same degree of urgency are stored in reverse chronological order. An audible tone alerts the user to the existence of one or more alarm conditions. The system, upon prompting by the user, presents the alarms to the user for action.

The infusion pumping system is also responsive to remote or biofeedback instructions to alter a planned infusion program.

DESCRIPTION OF THE DRAWINGS

FIG. 35 is a diagram showing the state of the pumping system after various alarm conditions;

FIG. 36 is an alarm priority table;

FIGS. 38–42 are flow charts illustrating the biofeedback/ remote programming system.

DETAILED DESCRIPTION OF THE INVENTION

Figure 1:
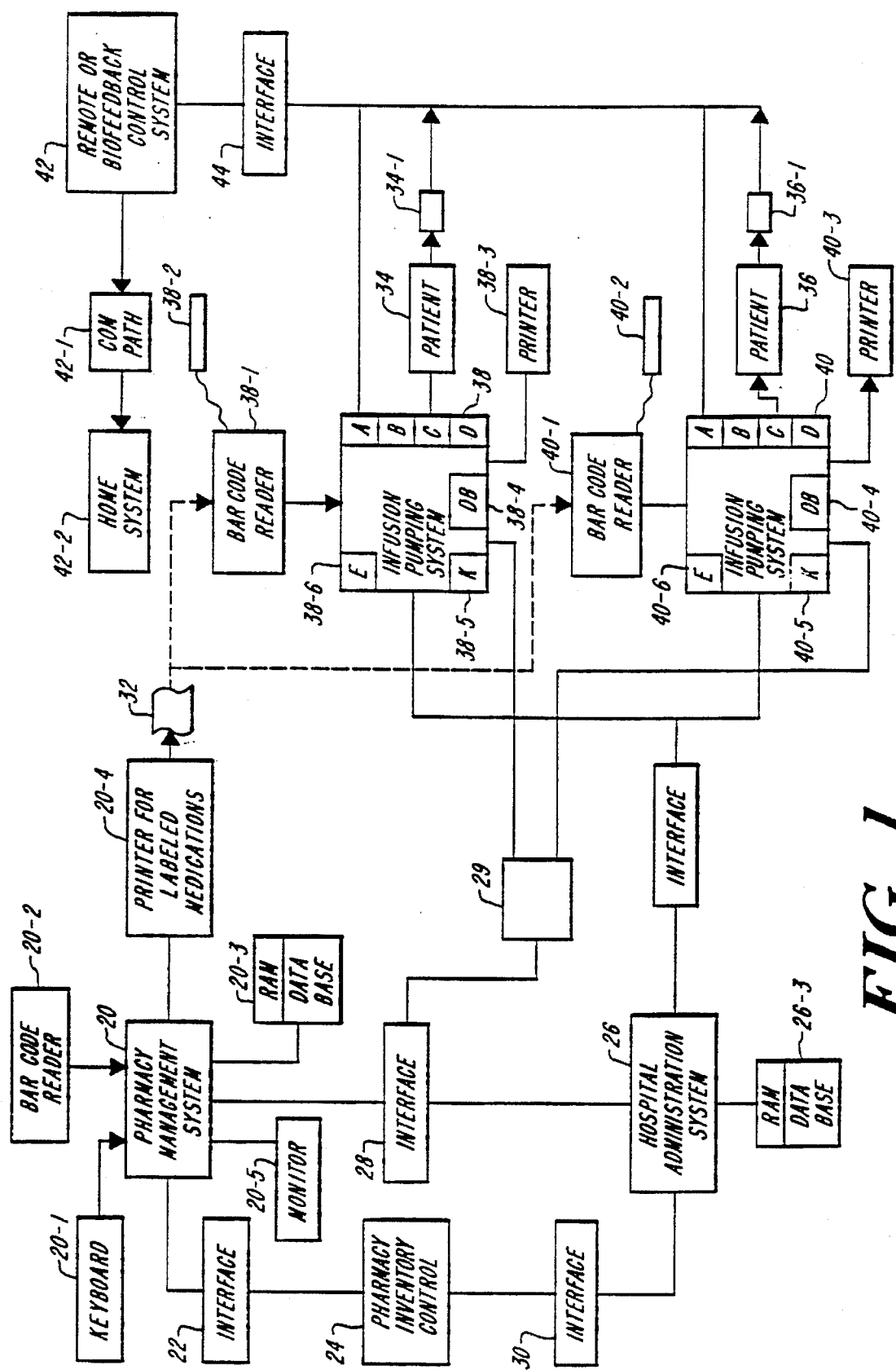
FIG. 1 shows a schematic block diagram of the fluid management and pumping system of the present invention.

The present invention is shown generally in block diagram format in FIG. 1. A pharmacy management system 20 includes a computer keyboard 20-1 for input, bar code reader 20-2, database 20-3 and a printer 20-4 for generating a bar coded label to be placed on the container for an intravenous solution made up by the pharmacy of a hospital or clinic. Since the pharmacy management system 20 accurately tracks the quantities of drugs used, it may communicate through an interface 22 with the hospital's existing computer based pharmacy inventory control system 24 for the exchange of hospital specific inventory and drug labelling data.

A hospital typically has a pre-existing computerized administration system 26. The pharmacy management system 20 communicates through interface 28 with this pre-existing hospital administration system 26. The hospital administration system also communicates through an interface 30 with the hospital's pre-existing inventory control system 24.

Labels 32 for infusion formulation generated by the pharmacy management system 20 from keyboard bar code input of prescriptions are transported to the appropriate patient 34 infusion pumping systems 38 and 40 (as shown in the above referenced patent) as shown by the dotted lines in FIG. 1. While only two patients 34, 36 and associated pumping systems 38 and 40 are shown in FIG. 1, each hospital will generally have many such patients. Each infusion pumping system 38, 40 includes a bar code reader 38-1 and 40-1 coupled into the database of the pump through a parallel data port or an RS-232 serial port shown in Epstein, et al. The label is read by the bar code reader and all the information on the label is transferred to the infusion pumping system in the same manner as manual data entry occurs.

The infusion management system also includes a remote/ biofeedback control system 42 which operates through an interface 44. In biofeedback applications information is sensed by patient sensors 34-1 and 36-2, such as blood pressure or glucose levels, and instructions are sent to the infusion pumping systems 38, 40 to alter the planned program of infusion in response to the sensed information. With the remote capabilities of control system 42, a patient may remain at home. Instructions for programming an infusion pumping system are sent over a phone line communication path 42-1 to a home system 42-2 of pumping systems by the control system 42.

The pharmacy management system 20 may be described with more detail by reference to the flow charts of FIGS. 2–29. Specifically, the pharmacy management system provides a program for encoding infusion delivery instructions for intravenous solutions in a bar code format. The system takes the operator through a series of screens and menus which request the information necessary to program the infusion pumping system. A final screen summarizes all the data that has been entered, requests confirmation from the operator, and provides the option for making a label. The delivery instructions are printed in bar code format as well as in human readable format on the label.

The system can be run on commercially available computers. Preferably, the system includes a monitor 20-5 for displaying the data screens and a keyboard 20-1 for entering the data.

Figures 1A, 2:
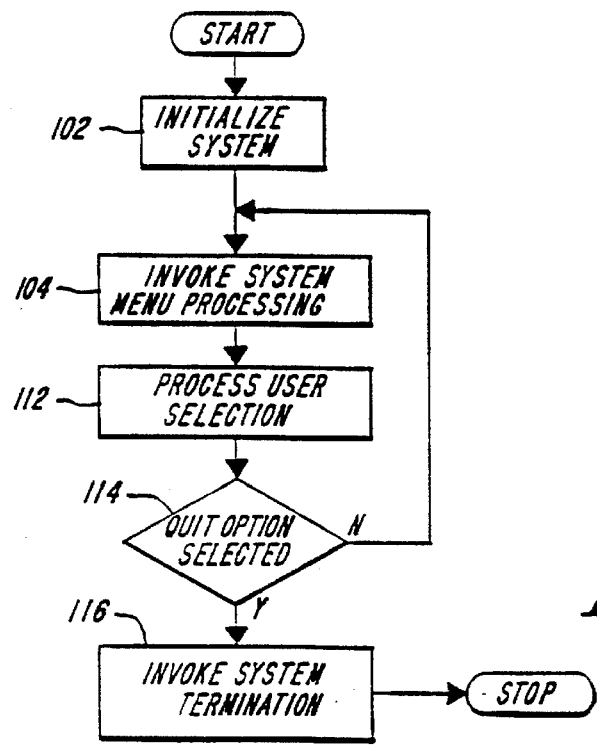
FIG. 1A shows a bar coded label of the present fluid management system.
FIGS. 2–29 are flow charts illustrating the pharmacy management system of the present invention.
Figure 3:
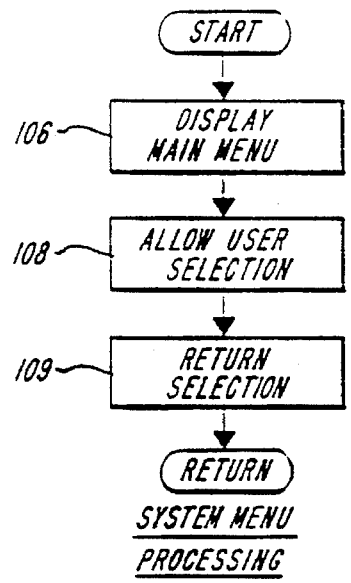

The flow chart of FIG. 2 shows the overall operation of entering data for each intravenous solution to be infused into a patient. The encoding program is initialized in step 102 by booting up the computer with the pharmacy management system installed in the computer's memory and typing an appropriate command including calendar entry. The system invokes a system menu processing routine in step 104, which gives the user a choice of several tasks to perform. The system menu processing routine is described in greater detail by reference to the flow chart of FIG. 3. The system displays the main menu 106. The main menu displayed to the user allows the choice of editing previous labels, all on specific patient scripts, processing new entries, printing all on a range of labels, generating a report, archiving the database, batch delete or restoring the database. The user makes a selection 108 and the system returns the selection in step 109 and returns processing to the main program. The user's selection is then processed in step 112 in FIG. 2. After the user's selection has been processed, the system gives the user the option of quitting or performing another task. If the user wants to perform another task, the system returns to the step of invoking the system menu processing in step 104 to allow the user another selection. If the user quits, the system invokes system termination, as shown by block 116.

Figure 4:
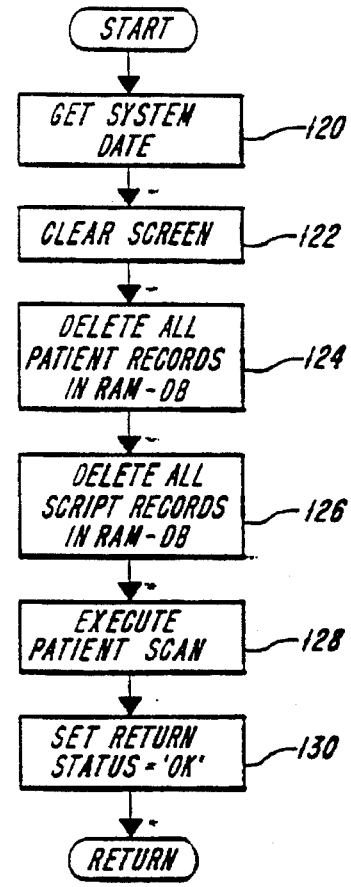
Figure 5:
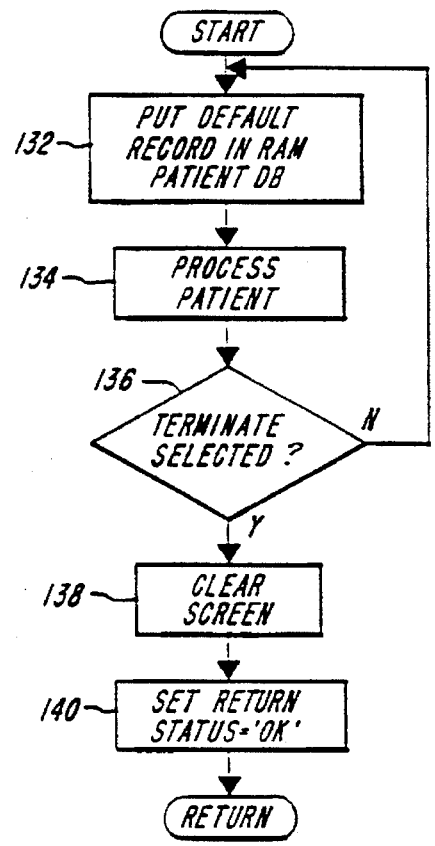

The task of processing previous entries is shown in the flow chart of FIG. 4. This task allows the user to call up infusions that have been previously entered and are due to expire on a specified data. The user then determines whether the infusion should be renewed. If the infusion is to be renewed, the system saves the patient's records. As shown by the flow chart of FIG. 4, this routine retrieves the date from the system in step 120. It clears the screen in step 122 and a work space in RAM, as shown by steps 124 and 126. The system then executes a patient scan 128, in which it searches for infusions due to expire that date. It displays each infusion record on the screen and provides the user with the option of renewing the infusion by printing a bar coded label. After the scan is complete, and all bar coded labels printed, the routine sets return status to "OK," enabling processing to return to the routine of FIG. 2.

The processing of new infusion entries is shown by the flow charts of FIGS. 5–17. The system's first step is to put all existing records, including records saved in the "processing previous entries" routine, in a workspace in RAM 20-3 in step 132. The system then calls a routine to process a patient record 134, shown in more detail in FIGS. 6 and 7. The system will display a screen asking for patient identification data in step 150 and will set the data mode to allow input in step 152. The patient may be identified by name or identification number. If the patient has previously been recorded in the system, entering one of the patient's name or identification number will cause any other patient data in the patient's record stored in RAM 20-3 to appear on the screen. The patient identification screen also contains data fields requesting or displaying data on the patient's room number or other location identifier, total number of intravenous solution labels required by the patient, the patient's physician, and physician identification number. Once all the patient identification data corresponding to label fields in a typical label as shown in FIG. 1A has been correctly provided, the special function key may be depressed to enter this data and display the next screen 154. The patient data remains displayed in a window at the top of the monitor while the remaining infusion data on the subsequent screens is entered. If the system includes a color monitor, the patient identification screen may change to a different color in step 156, to indicate that it has been entered.

Each patient can receive a number of different drug regimens. Each regimen refers to the delivery instructions for a solution of drugs contained in one intravenous container. As in step 158, the system sets the regimen count to zero. The system then increments the regimen count, in step 160. For the first drug regimen, the regimen count is 1. The system clears a work space in RAM, in step 162. The system then makes a control number, in step 164. The control number is for the pharmacy's use in keeping track of all the intravenous solutions it formulates. The next step 166 initializes a default prescription (or script) 166. For example, certain data such as the keep vein open (KVO) rate is often the same regardless of the drug. In addition, the expiration date is usually set for one day later but can be adjusted by a higher level of authorization. This data is placed into the system as default data, but it can be changed by the user during the next step of processing the script in step 168.

Figure 8:
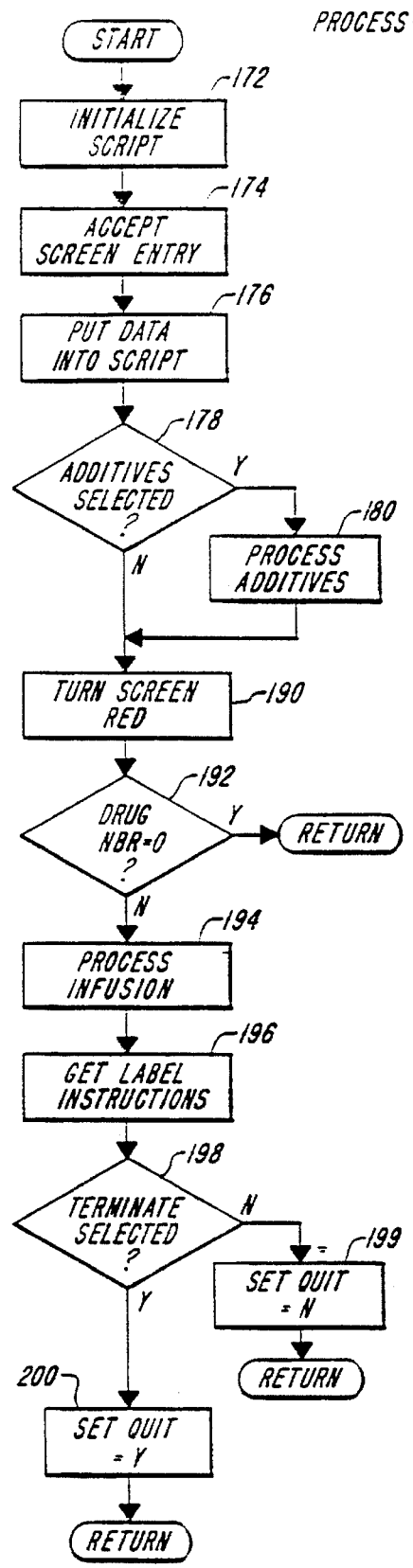
Figure 9:
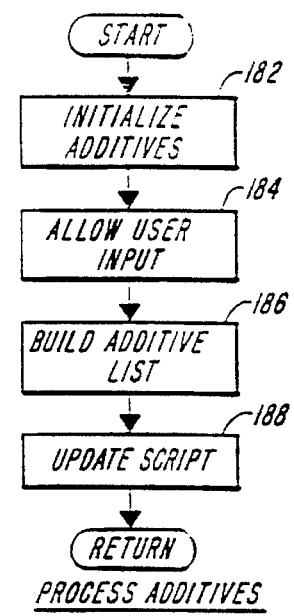

The procedure involved in processing each prescription is shown with more detail in FIGS. 8–16. As shown in FIG. 8, the first step 122 initializes the script causing the drug entry screen to appear. The system accepts entry of data in each of the data fields in the screen. The data fields include the drug regimen number, the prescription date, the expiration date, the prescription number, the pharmacy control number, and the drug name, drug mnemonic, and drug identification number, and the drug concentration in a carrier solution. These correspond to fields shown in a sample label in FIG. 1A. When the user enters a drug either by name, mnemonic or number, the remaining unentered data previously set up as default data, will automatically be supplied by the system.

Figure 10:
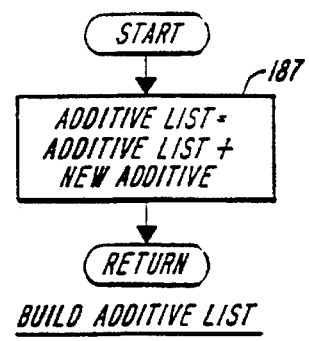

The system then displays a screen asking the user if additives are desired in step 178. If the user selects additives, the additives are processed in step 180 as shown by the flow charts of FIGS. 9 and 10. The system initializes the additives by displaying an additive screen in step 182. User input in step 184 allows the user to enter the additives desired. The system builds an additive list in step 186 simply by adding a new additive to the list in the routine as shown in FIG. 10. The system then updates the script in step 188 to include all the additives. Once all the additives have been processed, the system returns to the routine of FIG. 8, displays the data in a window of a different color to show that all the prescription medication data has been entered in step 190, and continues to the step of processing the infusion in step 194.

Figure 11:
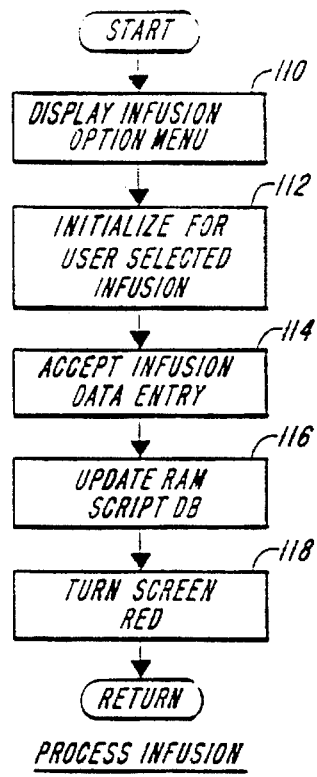

The steps of processing the infusion are shown in FIG. 11. The system displays a menu in step 110 for choosing the type of infusion. The infusion types are continuous, maintenance, and intermittent. If continuous infusion is selected, the screen will display data fields for the dose rate and the dose volume and a menu for the selection of the appropriate units. If maintenance infusion is selected, the screen will display data fields for the maintenance rate and total volume and a menu for the selection of the appropriate units. If intermittent infusion is selected, the screen will display data fields for the volume per dose, the time per dose, the dose rate, the dose frequency, the total number of doses, and whether a dilution or a syringe is desired. Again, the screen will also allow the selection of the desired units. If dilution is selected, the screen will display data fields for the entry of the dilution rate per dose and volume per dose. After all this data has been entered, the user hits a special function key which allows the system to update the script and store the data in step 116. This data may also be displayed in a red window in step 118.

Figure 12:
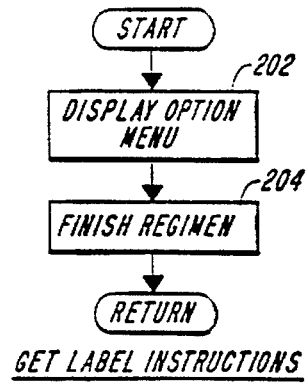

At this point, all the necessary data for the infusion has been entered into the system. The next step is to generate a label containing the data in both bar code readable and human readable format. The system gets the label instructions in step 196, as shown in FIG. 8 and in flow charts of FIGS. 12–17. The first step of the flow chart of FIG. 12 is to display an option menu in step 202. The options are to make a label, skip making a label, edit a label, or terminate. After a menu option is selected, the processor moves on to the next step of finishing the regimen in step 204.

Figure 6:
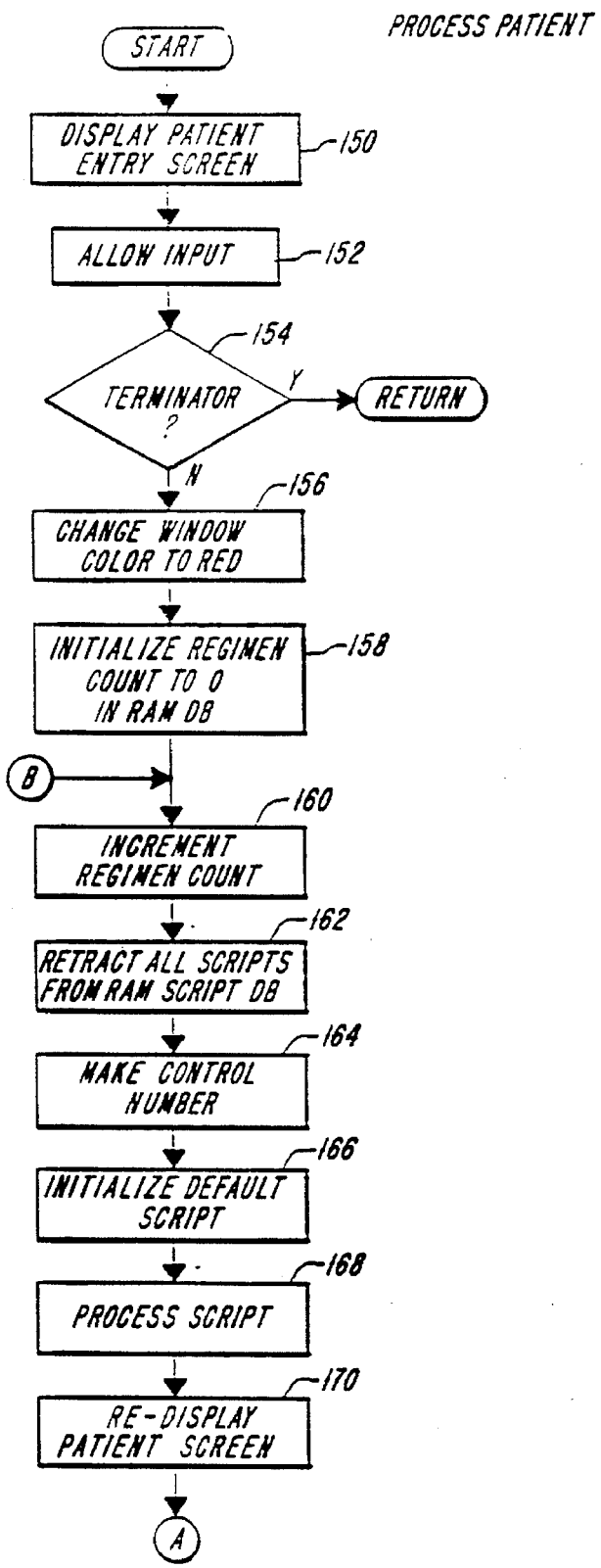
Figure 7:
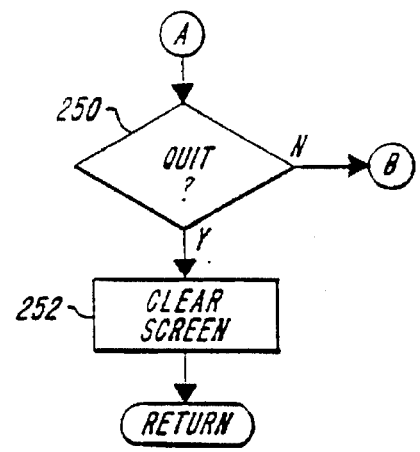
Figure 13:
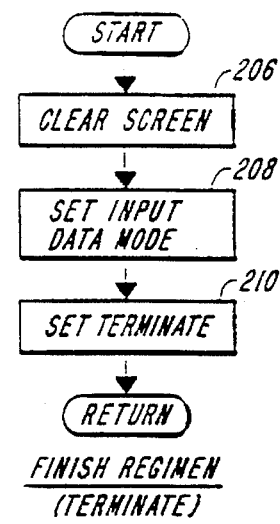

If the terminate option is selected, the system, as shown in FIG. 13 clears the screen in step 206, sets the data mode to input in step 208, allowing the user to start on a new patient or prescription, and sets the system to terminate the present infusion entry in step 210. Processing is returned to step 198 in FIG. 8. Since termination has been selected, the system quits in step 200. Processing then returns to step 168 in FIG. 6. Since "quit" has been selected, processing returns as shown in FIG. 7 to the main program of FIG. 2 and finally terminates in steps 114, 116.

Figure 14:
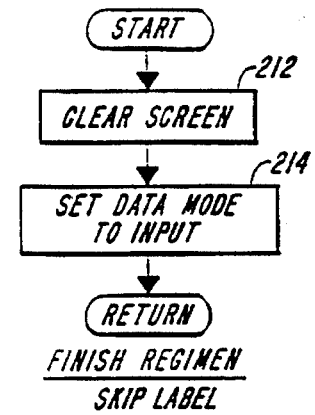
Figure 15:
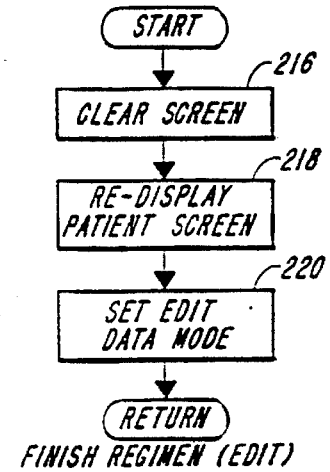

If, instead, the option to skip making the label is selected, then the system as shown in FIG. 14 clears the screen in step 212 and sets the data mode to input in step 214. This allows the user to continue inputting data on the same patient. If the user elects to edit the data, as shown in FIG. 15, the system clears the screen in step 216, redisplays the patient screen in step 218, and sets the data mode to edit in step 220, allowing the user to edit the data relating to the current patient or prescription. This allows the user to make any changes that may be necessary.

Figure 16:
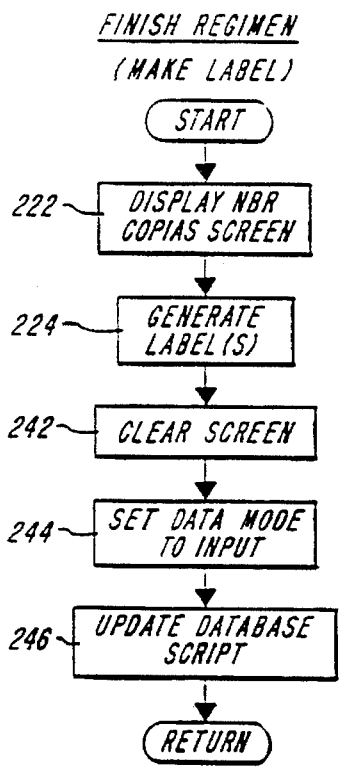
Figure 17:
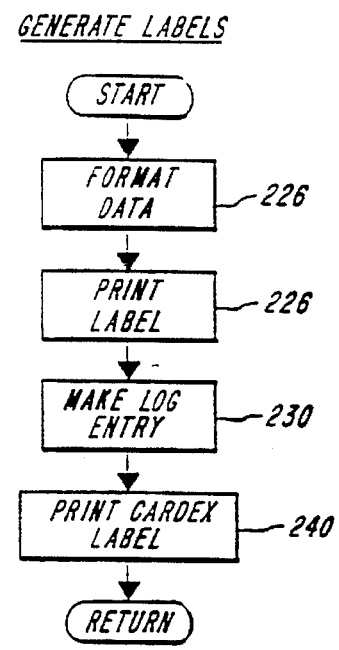
Figure 18:
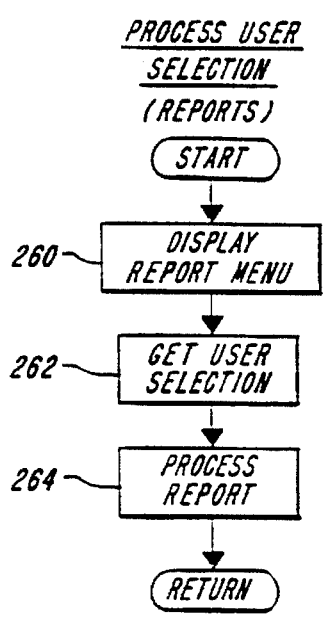
Figure 19:
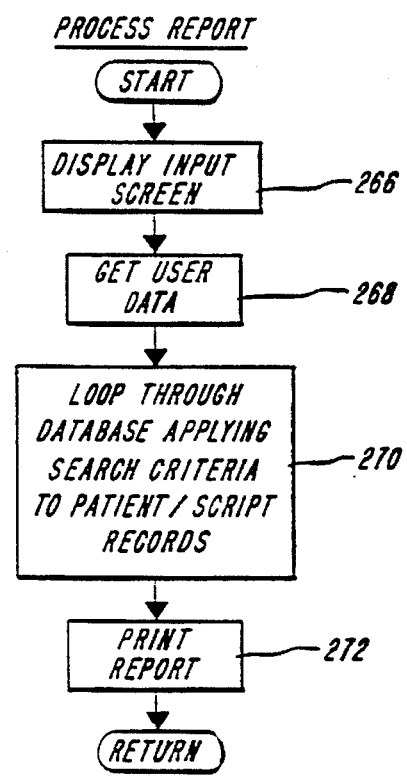
Figure 20:
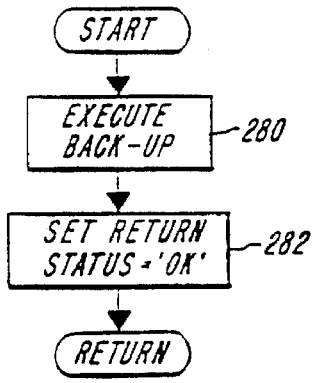
Figure 21:
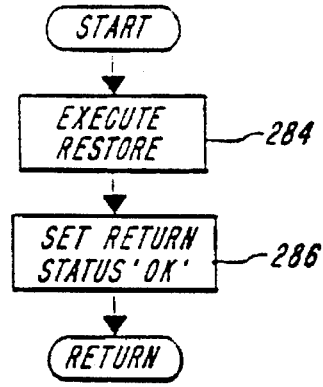

If all the data has been correctly entered, the user can make a label, as shown in FIG. 16. The system displays a screen in step 222 to allow the user to set the number of copies. The system then generates labels in step 224, as shown in FIG. 17. The system formats the data in step 226 in bar code readable and human readable form. The system then prints the label in step 228. A conventional bar code printer may be used. The bar code symbology preferably is three of nine (39), an alpha/numeric encoding system with a high reliability rate (internal check character) as recommended by the Health Industry Business Communications Counsel.

The system then makes a log entry and a label in step 230 and prints an additional label in step 240, for example, to attach to the patient's chart. The system then clears the screen in step 242, as shown in FIG. 16, sets the data mode to input in step 244 to allow further input of data, and updates the prescription database in step 246 by storing the completed prescription in the database. Processing is then returned to step 198 of FIG. 8, where the user is given the option of terminating the input on the present patient or continuing with the present patient by processing a further prescription.

If the user selects termination, in step 198, quit is set to yes in step 200. Processing is returned to step 170, as shown in FIG. 6 and the patient screen is redisplayed. If quit, as shown in step 250 of FIG. 7 is selected, the screen is cleared in step 252. Processing returns to the routine shown by the flow chart in FIG. 2. If the user does not select termination, in step 250 processing returns to step 160 of FIG. 6. The regiment count is incremented by one. This allows the user to process a second prescription for the same patient. The system then goes through the identical steps for any desired number of prescriptions for the particular patient. If the user has finished processing scripts for the patient, the system sets a "return" status, which allows processing to return to the main menu.

A further user selection allowed by the system in the routine shown in the flow chart of FIG. 2 is the making of a patient report. The flow charts of FIGS. 18 and 19 describe this routine. When this option is selected, a report menu is displayed in step 260. The system gets the user selection in step 262 and processes the report in step 264, as shown more fully in FIG. 19. The system displays an input screen in step 266, gets the user's data in step 268 and loops through the database in step 270, applying the search criteria input by the user in the previous step 268 to the patient script records. The system then prints the report in step 272. Alternatively, the system could interface with the hospital administration system 26, as shown in FIG. 1, and send the report to the hospital administration system.

Figure 22:
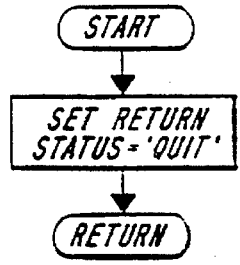

Typical examples of report generation include a summary over a specified time of all drugs labelled for a patient. Two other options provided in the menu of FIG. 2 are to archive the database or to restore the database. Archiving the database is shown in the flow chart of FIG. 20. The system executes a backup in step 280, generally by storing the database on a floppy disk and returns in step 282 to the main menu. The opposite procedure, shown in FIG. 22, is the restoring of the database to the system. In this routine, the system executes a restore in step 284, generally reading the database from the floppy disk into the storage on the system and returns in step 286 to the main menu.

The system also includes a stored drug table in RAM 20-3. The drug table includes a list of all the drugs used or prescribed for patients in the hospital. The drugs may be stored by drug name, mnemonic, and identification number. The drug table may also include incompatibility data for the drugs. For example, if a solution containing a mixture of two drugs were to cause particles to precipitate, the drugs would be incompatible, since a solution with precipitates would not be suitable for infusion into a patient. The system checks the drug table upon entering new prescriptions for each patient. The drug table supplies some of the drug data to be included on the label. The drug table may be edited to change data on the drugs included in the database, or to add or delete drugs to and from the database.

Figure 23:
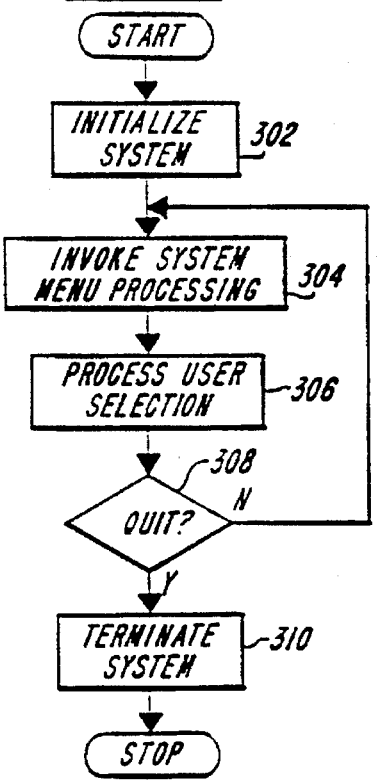

FIGS. 23–29 show the flow charts for the routines which allow entry, deletion, and editing of the data in the drug database. FIG. 23 shows the flow chart for the main routine. The first step 302 is to initialize the system, generally by typing an appropriate command on the keyboard. The system then invokes the system menu processing in step 304. The user can select from the choices of loading the drug file, saving the drug file, printing a drug table, entering drug data, editing drug data, and deleting drug data. After the user makes a selection, the system processes the user selection in step 306.

Figure 24:
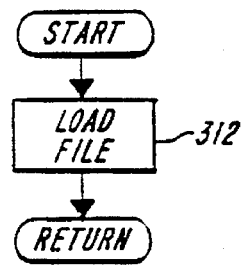

To work on the database, the user must first load the drug file, as shown by the routine of FIG. 24. The system loads the database in step 312. The system then returns and asks the user whether the user wishes to quit or continue, as shown by step 308. If the user wishes to continue, the system menu processing is once again invoked in step 304 allowing the user to make a further selection.

Figure 27:
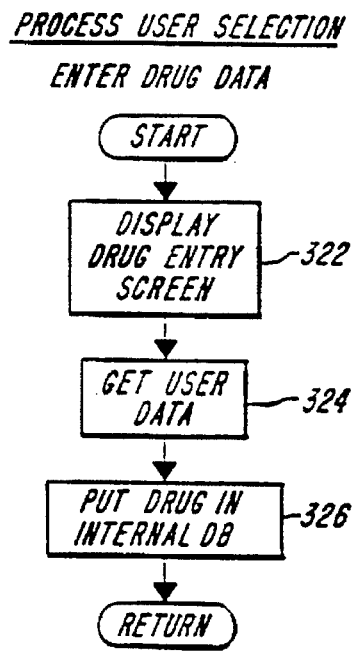
Figure 28:
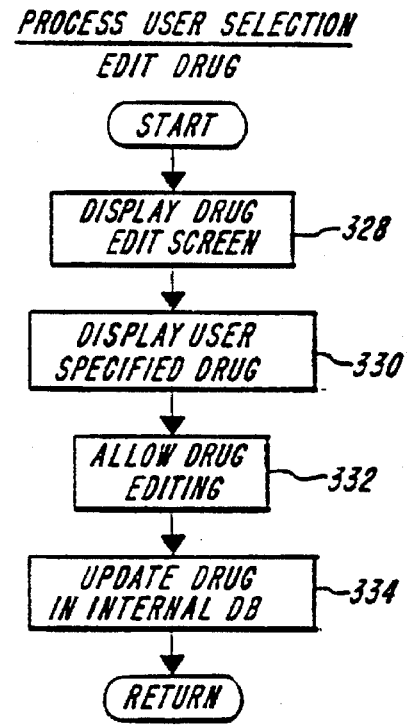
Figure 29:
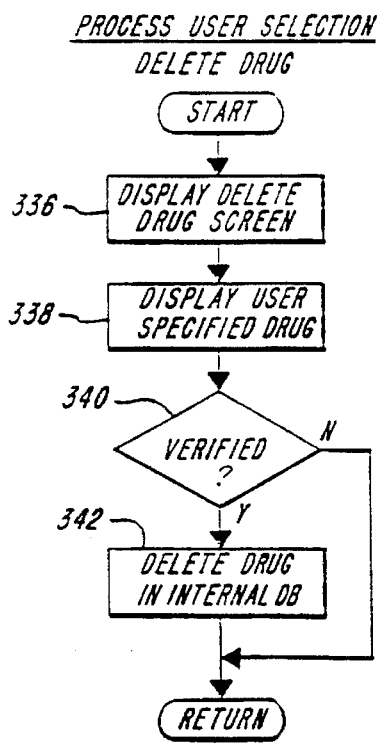

New drug data is entered by the routine shown by the flow chart in FIG. 27. The system displays a drug entry screen in step 322. The user enters data in step 324, and the system puts the entered drug data into the database in step 326. If the user selected the option of editing the drug data, the routine shown in FIG. 28 is followed. The system displays a drug edit screen in step 328. The drug edit screen requests the user to specify a particular drug and the system displays the data contained for this drug in step 330. The user may then edit the data regarding the specified drug in step 332. After the user has completed editing, the system updates the internal database by storing the edited data. If the user selects the option of deleting a drug from the database, the routine shown in FIG. 29 is followed. The system displays a delete drug screen in step 336. The user selects a drug to be deleted. The display shows the drug specified by the user in step 338. The system then asks for verification that the drug is to be deleted in step 340. If the user chooses no, the drug will not be deleted. If the user chooses yes, the drug will be deleted from the database in step 342.

Figure 25:
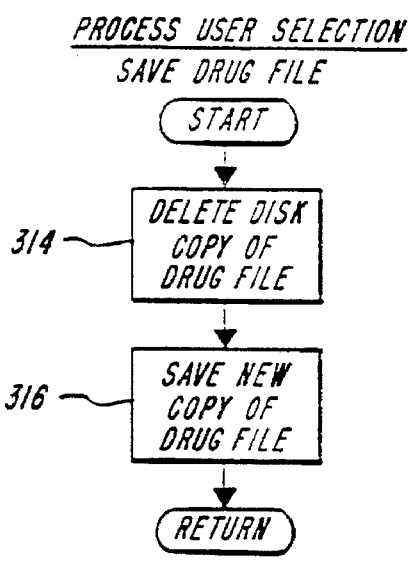
Figure 26:
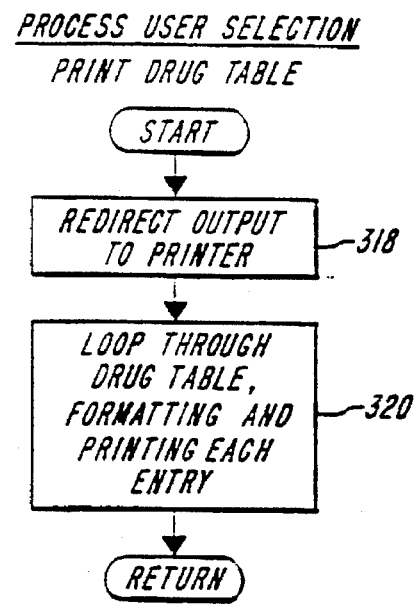

The flow chart of FIG. 25 allows the archiving of a drug database that has been recently changed. If this option is selected, the system deletes the old copy of the drug database in step 314. The new copy of the drug database is saved in step 316. The user can also print the drug database, as shown by FIG. 26. If the user selects this option, the system redirects the output to a printer in step 318. The system then loops through the drug database, formatting and printing each entry in step 320.

After each prescription label has been generated by the pharmacy management system, the label is placed on the bag containing the solution to be infused. The bag is carried or transported by the hospital's usual method to the patient's location. The delivery instructions printed on the label on the medication container must be inputted to the infusion pumping system. The flow charts of FIGS. 30–34 describe the process used to enter the data on the labeled medications by bar code reading.

Figure 30:
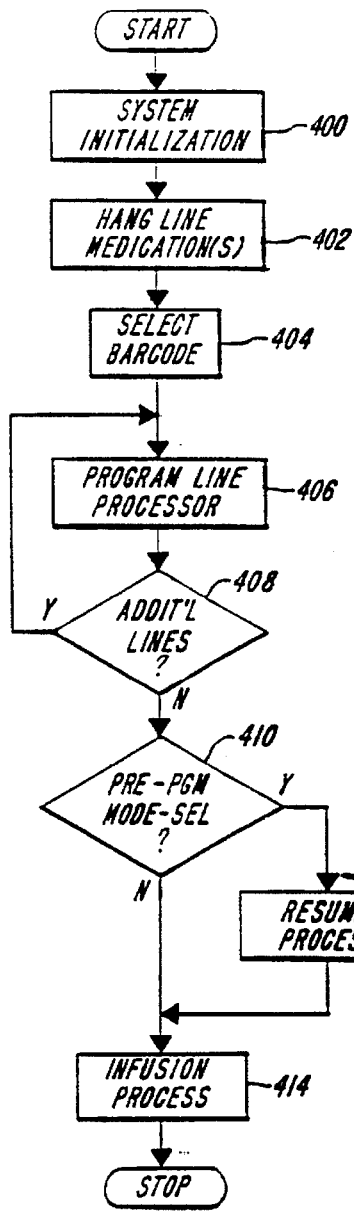
FIGS. 30–34 are flow charts illustrating data entry into the fluid pumping system of the present invention.

The infusion pumping system generally is a system similar to that described in the above-referenced patent to Epstein, et al. The system contains a housing in which is placed a disposable cassette containing plural input ports and a single patient output port. The medications are hung from a rack and tubing is run from the medication container to one of the input ports. In the prior art system, a nurse or other health practitioner programs the infusion pumping system with the necessary delivery instructions such as dose rate, total volume to be infused, and starting and stopping times. With the system of the present invention, this data has already been encoded on the bar code label attached to the solution container. As shown in FIG. 30, the user initializes the system in step 400, generally by turning on the infusion pumping device, which runs a self test procedure and is then ready to accept input. The user hangs the line medication or medications on the rack in step 402. The user selects the method of inputting the data to the system, either through the bar codes or manually through a keypad as in the prior art systems. If bar code entry is desired, the user depresses an appropriate key on the keypad in step 404. The user then programs the line processor in step 406 by wanding the bar coded data with a bar code wand 38-2, 40-2.

The button corresponding to the connect line (A–D) is pushed to correlate that regimen to the appropriate line. The infusion pumping system generally contains plural input lines. If other solutions are to be infused on additional lines, the delivery instructions for those solutions may be entered in the same manner in step 408. After all lines have been programmed, the system gives the option of selecting a pre-programmed mode in step 410. The pre-program mode allows the start of the infusion program to be delayed. This is a useful option if the user is expecting the patient to arrive from, for example, an operating room and desires to get the infusions set up in advance. If the pre-program mode is selected, the system will resume the realtime process in step 412 at the appropriate time. When the start time arrives, the system controls the infusion process in step 414 according to the programmed delivery instructions.

Figure 31:
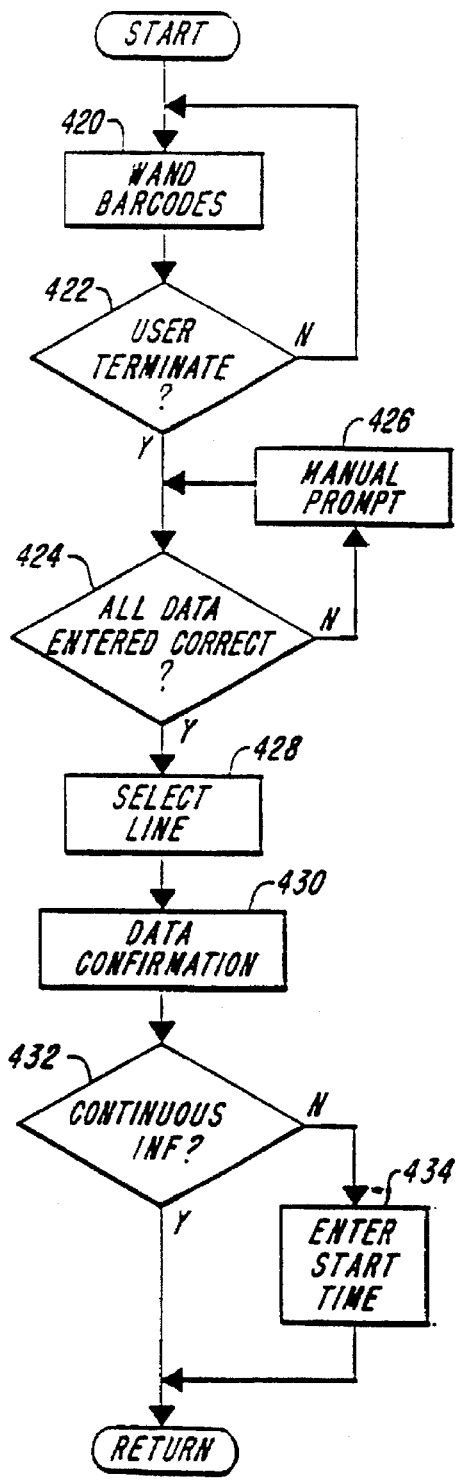

FIG. 31 shows the procedure for programming each infusion line, as shown by step 406 of FIG. 30 in more detail. If bar code input has been selected at step in step 404, the user inputs the bar coded data through a conventional bar code reader 38-1, 40-1. Generally, the user passes a bar code wand or pen 38-2, 40-2 across the coded data, from right to left or left to right. All the lines must be read. A validity check is made on the data read by the bar code reader, into the infusion pumping system and a "good" beep is provided if the data falls within expected ranges. If the data is not accepted by the bar code wand, the system will respond in a manner which is readily distinguishable from the "good" beep. Data not accepted by the bar code reader is to be wanded again. If the data continues to be unreadable, the data may be entered through the keypad of the infusion system 38, 40.

The infusion pumping system 38, 40 includes a database memory 38-4, 40-4, a small screen, generally a liquid crystal display, which prompts the user for the data to be wanded or entered through the keypad. The system will prompt the user for the user's personal identification number. This data may be provided in bar code format on, for example, a nurse's badge. The system will then request entry of the data contained on the solution label. Finally, the patient identification data must be entered. This data may also be in bar code format on the patient's chart or bracelet. The system verifies that the patient identification from the chart or bracelet matches the patient identification on the solution label and provides a mismatch indication.

Figure 32:
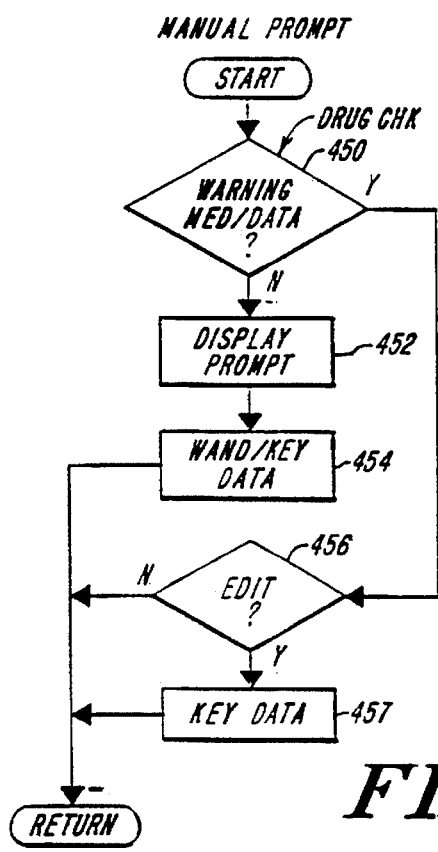

After all the data has been entered, the system checks to see whether all the data has been entered correctly, as shown by step 424. If not, the system prompts for any missing data in step 426. The manual prompt routine, as shown in FIG. 32, runs through all the necessary data in step 450. For any missing data, it displays a prompt in step 452 requesting entry of the data. The user wands or keys in the data in step 454. At this point, the system may also check the prescribed drugs against the patient's record for allergies to the drugs that have been prerecorded in databases 38-4, 40-4. If any drugs to which the patient is allergic have been prescribed, the pumping system displays a message so informing the user.

Figure 33:
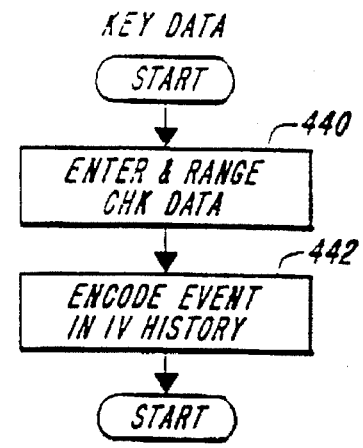

The user may edit the data to change the regimen in step 456. FIG. 33 shows a flow chart for the routine the system uses when data is entered by keyboard 38-5, 40-5. The data is entered and the system range checks the data in step 440. Then, the system encodes the event in an I.V. history in step 442 that is maintained for each course of infusion therapy.

Figure 34:
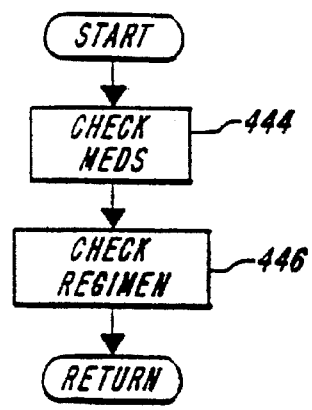

After all the data identifying the medications and the infusion data are entered, the system requests the user to select an input line in step 428, as shown in FIG. 31. Finally, the system runs through a data confirmation check in step 430. As shown in FIG. 34, the system checks all the medications in step 442, by displaying the medications to the user who confirms by depression of an appropriate key on the keypad. The system then displays the drug regimen to the user in step 446, who again confirms the drug regimen by depression of the key on the keypad for that purpose (38-5, 40-5). The user can make any changes to the medications or the regimen at this point by manual entry through the keypad. In this manner, a safety check on the data contained on the bar code label is provided. Also, any changes to the infusion therapy can be made. Finally, the system checks if the infusion is to be a continuous or maintenance infusion in step 432. If not, the system prompts the user for the entry of a start time in step 434, as shown in FIG. 31. The above procedure is repeated for each solution to be infused on each of the input lines provided on the infusion pumping system.

During the administration of an infusion, various alarm conditions can occur. Alarms can range from a simple audible tone to call the operator back to, for example, start an infusion, to a problem which renders it impossible for fluid to be delivered to the patient. More than one alarm condition can occur at the same time. The present invention provides an improved alarm handler. The alarm handler is best described by reference to FIGS. 35 and 36. Each of the various alarms is assigned a priority which is used for displaying the alarm conditions to the operator for clearing. When more than one alarm exists at a single time, the alarms are displayed in order of priority, highest priority first. If a subsequent alarm has a higher priority than an existing alarm, the subsequent alarm will be handled before the earlier alarm. If two alarms have the same priority, the most recent alarm will be handled first.

The alarms may generally be classified into three distinct types: warnings, pumping alarms, and fluid delivery alarms. Fluid delivery alarms have the highest priority, warnings the least. Warnings do not change the state of the infusion pumping system and merely alert the operator to a condition. Pumping alarms relate to the ability to pump on one or more of the input lines and may change the state of the device by suspending pumping on one or more of the lines. Fluid delivery alarms occur when fluid cannot be delivered to the patient or when there is the possibility of free flow to the patient.

When an alarm occurs, its time of occurrence is recorded and it is placed on an alarm stack. When the operator arrives to service the alarms, the alarms are displayed in order of highest priority first and in reverse chronological order for alarms of the same priority. If one or more lines of the pump have been placed on hold or pumping has been stopped on all lines, pump operation will not resume until the entire alarm stack has been displayed to the operator and serviced if necessary.

The table of FIG. 36 displays the alarm priorities of the preferred embodiment. The highest priority alarm is the cassette unlocked alarm. When the cassette is unlocked, free flow of a fluid to the patient may be possible. Therefore, all infusing lines are placed on hold immediately when the cassette is unlocked.

The second priority alarm is a pump failure. The effect of a pump failure alarm is to stop pumping on all lines immediately. Service may be required to repair a pump failure.

The third priority alarm occurs when an occlusion in the patient output line is detected by the on pump pressure system. This alarm is not detectable unless one or more lines are infusing. The effect is to cause all infusing lines to be placed on hold until the occlusion is cleared.

The fourth priority alarm is a possible full collection bag. The collection bag is used when the pump has detected air in the one of the infusing lines or an occlusion in one of the infusing lines and is attempting to purge the infusing line by diverting to the collection bag. Detection of a possible full collection bag causes all infusing lines to be placed on hold until the condition is cleared.

The fifth priority alarm occurs when air or another occlusion occurs in the primary fluid input line. Generally one of plural input lines is designated the primary input line. This alarm is generated after a few pump strokes. When this condition is detected, the system first attempts to purge the line with a few pumping strokes, diverting output to the collection bag if the condition does not clear up.

The sixth priority alarm relates to air or an occlusion detected in one of the remaining input lines. This alarm causes the line with the occlusion to be placed on hold. If all of the secondary input lines are placed on hold, pumping on the primary infusion line continues at a keep-vein-open rate.

The seventh priority alarm occurs when the pump is unable to pump at its programmed rate. The alarm is generated when, after several sequential "catch-up" pump cycles have occurred, the pumping rate remains less than the programmed rate. This alarm causes the primary input to infuse at the pre-selected keep-vein-open rate while all the other infusing lines are placed on hold.

The eighth priority alarm is a possible empty container alarm. This alarm is a warning, so actual pumping operation will continue.

The ninth priority alarm is a callback request. This alarm also is a warning. It is generated whenever an intermittent infusion is started or stopped.

Several other warnings may occur, but are not generally given a priority and placed on the alarm stack. The system alerts the operator, by producing an audible tone, that the battery voltage is low if the system is powered by a battery. Battery operation is advantageous when a patient must be moved from one location to another with the infusion continuing during the move. Another audible alarm is generated when one of the infusing lines has been manually placed on hold. After two minutes, an audible tone alerts the operator that the line is still on hold. Finally, an audible tone alerts the operator whenever the pumping system is transferred to battery operation.

FIG. 35 is a state diagram showing the states that the infusion pumping system is placed in by programming in the on board computer after the occurrence of one or more alarms. Each state is represented by a of the pumping system. The zero states box 502 labeled RUN refers to normal pumping operation. Box 504 labeled LINE HOLD refers to the one state in which one or more but not all of the pumping input lines have been placed on hold. The box 506 labeled HOLD KVO refers to the two state in which all the lines have been placed on hold except for the primary line, which continues to pump at the keep-vein-open rate. The box 508 labeled HOLD ALL refers to the three state in which all lines have been placed on hold. Finally, the box 510 labeled STOP ALL refers to the four state in which pumping has been stopped completely.

When infusing, the system is normally in the RUN state 502. Arrows label each one of the nine alarm priorities. Each arrow shows the state to which the system goes upon occurrence of an alarm of a given priority. For example, the cassette unlocked alarm has priority 1. The arrow with the 1 beside it (this arrow also has 3, 4, and 5 beside it), leads to the state labeled HOLD ALL in box 508. Thus, upon occurrence of a cassette unlocked alarm, all lines are placed on hold. They remain on hold until the alarm is cleared by the operator (by locking the cassette in place). If the system is in the RUN state 502 and an empty container alarm occurs, the system remains in the RUN state, as shown by the arrow exiting and returning to the RUN box.

If the system is in the RUN state and a sixth priority alarm occurs, the system will place that line on hold and be in the LINE HOLD state indicated by box 504. If, while the system is in that state, a second alarm of sixth priority occurs, that line will also be placed on hold. The system will remain in the LINE HOLD state, as shown by the arrow exiting and returning to the LINE HOLD box 504. However, if all secondary lines generate sixth priority alarms, the system will go to the state labeled HOLD KVO in box 506. This is not specifically shown in FIG. 35.

Each possible alarm condition is designated by a bit in the processor's storage. If the processor receives a signal that the alarm condition has occurred, the bit designated for that alarm condition becomes a "1." All the bits are passed through a filter which identifies all the "1" bits. These bits are ranked according to priority and time of occurrence and the user is alerted to call them up for display and action when a keyboard 38-5, 40-5 requested is made. The keyboard 38-5, 40-5 includes an override key whose function is to remove that bit from the memory and effectively reverse the process of FIG. 35.

In addition to the above alarms, the infusion pumping system performs a self-test upon installation. At this time, it tests for various error conditions and generates a screen display for any of these conditions which occur. These error conditions are tested only at this time. They are not included in the above priority table.

The pumping system includes an event recorder 38-6, 40-6 which generates a record in memory of all the "events" during a course of intravenous infusions, referred to as an IV history. The events include stopping, holding, or resuming an infusion on a particular line automatically or manually, and keyed to the time of occurrence. The IV history will also record unscheduled events, such as alarms or a transfer to battery power.

A complete IV history containing, in the preferred embodiment, events spanning up to 24 hours, can be generated and printed on printers 38-3 40-3 chronologically along with patient ID and drug ID. Alternatively, the operator can specify through the keyboard 38-5, 40-5 a range of events, such as the last twenty events, or a time period, such as the last two hours. The system will then generate and print an IV history only for the range or time period specified. Events pertaining to a particular patient when printed represent a retrospective medication administration record for that patient. This report can be appended to the patient's chart.

External events may also be recorded. For example, the operator may take the patient's blood pressure. The operator then enters the blood pressure data through appropriate keys on the keypad. The system records the blood pressure data and time it was entered and includes this event in the IV history.

Figure 39:
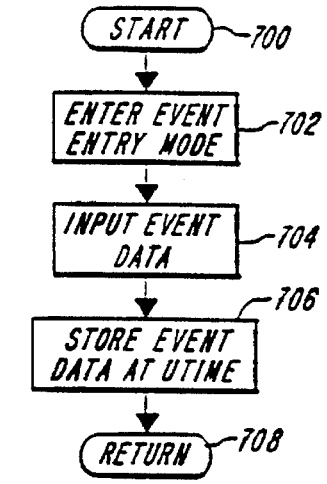

The entry of event data follows a flow chart of FIG. 39. From a start state 700, which functions as an event occurrence interrupt so that it can be entered with each event a keyboard 38-5, 40-5 request for event entry in step 702 initiates an event entry mode. Step 704 causes the event data to be received as such from keyboard and/or sensors and step 706 records the event and time in memory 38-4, 40-4. Step 708 returns to normal, pre-interrupt, processing.

The pumping system also is able to generate a record of the current device status. This record includes patient identification data, present infusion regimen data, the current status of each line, and the total amount infused on each line up to the current time. This report, when generated immediately after completion of regimen programming represents a prospective medication administration record for that patient and can be appended to the patient chart. This record may be updated each time a line is started, stopped, placed on hold, or resumed.

Figure 40:
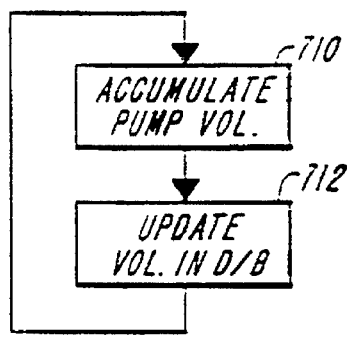

The entry of most of this data occurs from initial bar code reading. Pump volume data is recorded continuously during pumping using a volume accumulation update as shown in FIG. 40. In a step 710, volume for each line is accumulated for pump cycle commands. In step 712 this is periodically added to a volume record for each line in the database 38-4, 40-4 and step 710 resumed.

The pumping system includes a storage buffer to which the IV history or device status record is written. From there, the operator may direct the pumping system to generate a printed output on a local printer 38-3, 40-3 to, for example, be attached to the patient's chart.

Figure 41:
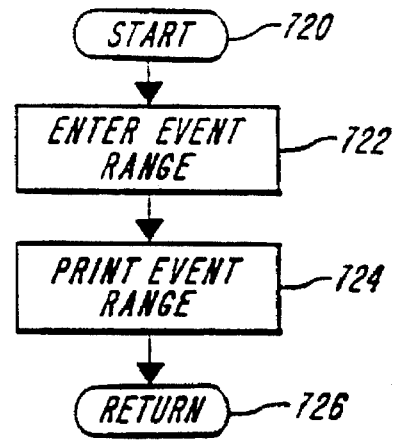

Printout of the IV history and device status uses a print routine of FIG. 41. From state 720, a step 720 is entered upon keypad command for printout. In step 722 the range of time events and the decision for an IV history or device status is made. In subsequent step 724, this record is assembled by the preset chronological format and sent to the printer.

Also, the operator may transfer the record directly through a serial port and mutltiplexer 29, or by manual transfer to the hospital administration system computer 26, via interface 28 as shown in FIG. 1. By making this data available to the hospital's main administration system 26, more accurate record keeping can be accomplished. For example, the patient can be billed for only the amount of solution actually infused. Also, the data can be transferred to the pharmacy management system 20 where it is stored in memory 20-3 for analysis of medication usage.

Figure 42:
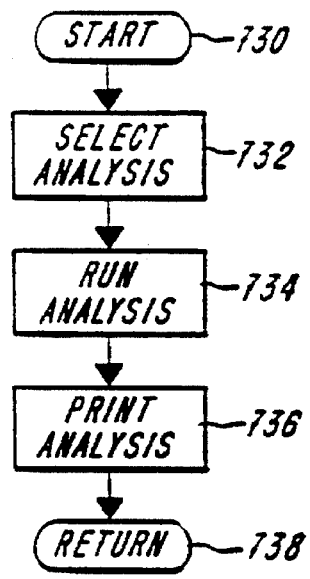

The analysis at either the pharmacy or administration systems 20, 26 follows the processing of FIG. 42. From a start state 730, an operator request for analysis causes step 732 to be entered. In step 732, the operator selects the type of analysis which includes: total drug usage by drug, by drug concentration, bottle size, total patient drug usage (by the same breakdown). In step 734, this analysis is run on the database 20-3, 26-3. In step 736, the result is printed in a step 736 and in step 738 the system returns to its prior state.

Figure 37:
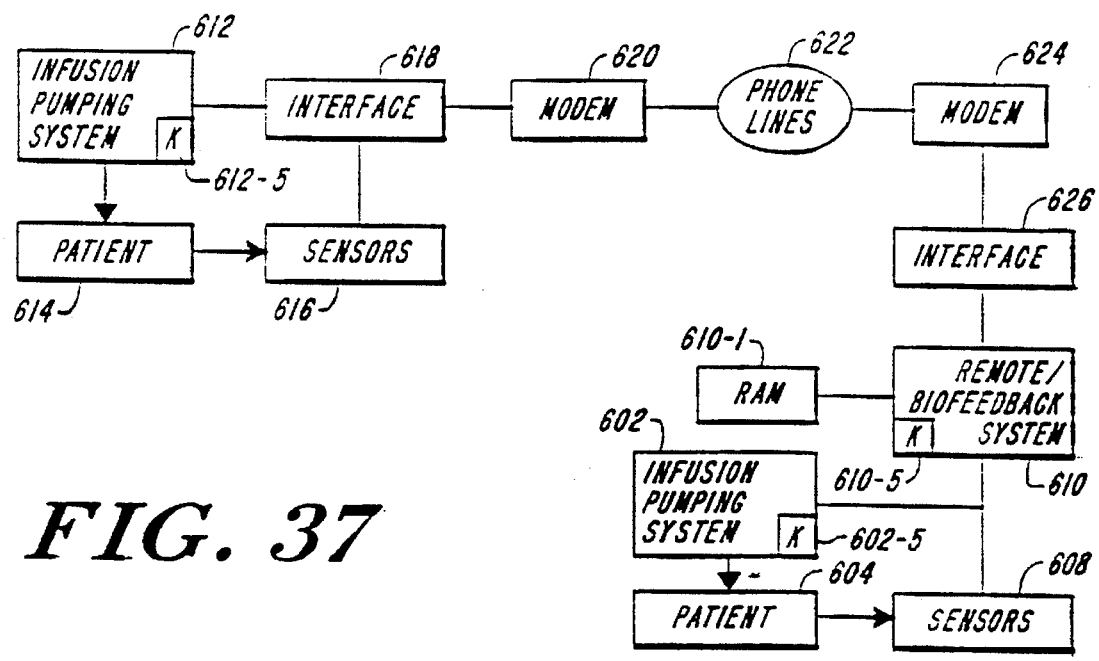
FIG. 37 is a schematic block diagram of the biofeedback remote programming system of the present invention.

Biofeedback and remote programming are implemented as different functions of a single auxilliary computer system 42 capability. This capability is shown more fully in FIGS. 37 and 38. Two infusion pumping systems 602 and 612, representing a network of infusion pumping systems, are shown in FIG. 37. Any number of pumping systems may be added. One of the pumping systems 612, as shown by FIG. 37, may be located away from the hospital in, for example, the home of patient 614.

A remote biofeedback network computer 610 functions as the remote controller for a network of pumping systems as shown in Epstein, et al. The computer 610 communicates with each pumping system generally through a serial port on each pumping system. Each infusion pumping system has data, such as that contained in the IV history record or device status record described above, available at the serial port for the remote computer 610. For example, an operator at the remote computer 610 can review all the alarm conditions on the alarm stack. In this manner, the remote system 610 monitors each pumping system 602, 612. The remote system also sends instructions to each pumping system over the network and in through the RS-232 serial port to alter the pumping state much like the bar code reader.

In biofeedback, or closed loop infusion applications, sensors 608, 616 monitor physiological conditions of the patient 604, 614, such as blood pressure, pulse rate, respiration rate, temperature, blood gases, and blood sugar levels. These sensors are either fully automated (as in FIG. 37) or alternatively, some operator intervention is instrumented as, for example, having the nurse measure the patient's blood pressure and enter the data manually via a keypad 602-5, 610-5, 612-5.

Figure 38:
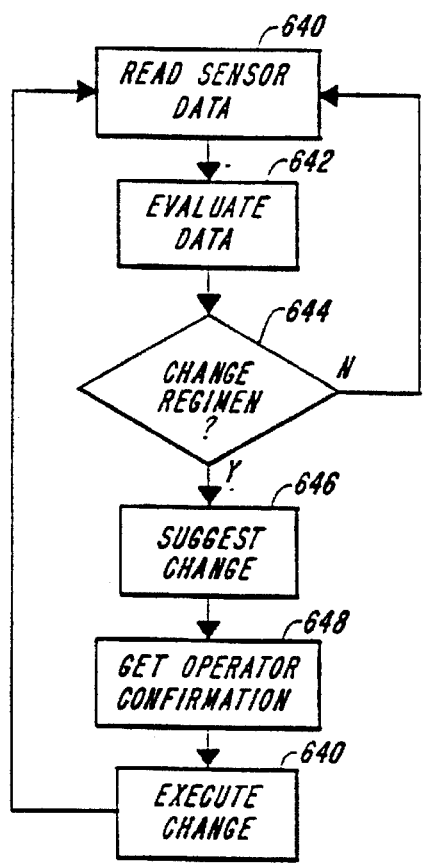
FIG. 38 is a flow chart illustrating the biofeedback/remote programming system.

The flow chart of FIG. 38 shows the steps taken by the system 610. The system 610 reads the sensor data in step 640 either directly from the sensor 608, as shown in FIG. 37, or from the infusion pumping system. The system evaluates the data in step 642 according to a pre-programmed set of conditions-result determinations in a memory 610-1. The condition-result analysis, which may be simple or a knowledge-based system (AI) determines if the infusion regimen should be changed in a step 644 as the result of the sensed conditions. If it determines a change is necessary, it suggests an appropriate change to an operator in step 646 and requests the operator confirmation in step 648. The operator can confirm the change, or override the system and make no change, or make a different change. Lastly, the system will execute any change to be made in step 650 by sending instructions directly to the infusion pumping system.

The network computer system 610 is locatable in a central area, such a nurse's station, where infusions for several patients are monitored. If an emergency condition develops, the nurse/operator can take immediate steps via the system 610 to help the patient. For example, an infusion can be immediately stopped, started, altered, or increased or a different drug added.

An example where biofeedback is useful is where precise alternations in the rate of flow of insulin are made in response to the patient's level of blood sugar. If the level gets too high, the rate of insulin infusion can be increased. Altering the rate of nitroprusside infusion in response to an inappropriate blood pressure is a further example.

The system is also capable of altering infusions on several lines in response to sensed conditions. For example, insulin may be infused on one line to lower a patient's blood sugar level. If the level gets too low, the insulin infusion can be stopped and a glucose infusion can be started on another line. As a further example, nitroprusside and dobutamine can be alternately infused, depending on the patient's blood pressure. As a further example, if a carrier fluid is infusing on one line and the operator wants to get medication on another line into the patient quickly, the medication on the other line can be started and the rate of infusion on the carrier's line increased.

Infusion pumping system 612 is shown in FIG. 37 configured for use in a patient's home. Some keypad functions on the pumping system 612 may be disabled to prevent accidental interference, but the system 612 is essentially the same in terms of infusion capability as is used in the hospital. An interface 618 is provided between pumping system 612 and a modem 620. Modem 620 allows communication to take place over a telephone line 622. At the hospital, a modem 624 and interface 626 to the network system 610 is provided.

In use, either the patient or a visiting medical technician hangs the medication and sets up the system in the home. The infusion can be started directly at the pumping system or by a signal sent by the remote system 610. The pumping system 612 initiates calls through interface 618 to the system 610 and the system 610 initiates calls to the pumping system via interface 626 using conventional automatic answer, automatic dial capabilities. A sensor 616, similar to sensor 604, may be included for biofeedback purposes, as described above.

The network configuration is useful for other tasks as well. For example, the network computer system 610 monitors the version of each pump and ensures that the delivery instructions encoded on the solution container by the pharmacy are appropriate for that version. Updating hardware and software is usually an ongoing process, so it is useful to have a back up check as to a safeguard.

The invention is not to be limited by what has been particularly shown and described, except as indicated by the appended claims.

We claim:

1. A system for infusing fluids into a patient comprising:
   means for infusing fluids into a patient in accordance with instructions to carry out a desired course of infusion therapy, including means for generating initial instructions to carry out the desired course of infusion therapy;
   means for sensing physiological conditions of the patient during the course of infusion; and
   means, in communication with the sensing means and the infusing means and located remotely from the infusing means, for monitoring the infusing means and for controlling the infusing means during the course of infusion in response to the sensed physiological conditions, including means for generating adapted instructions to carry out an adapted course of infusion therapy, means for displaying the adapted instructions to an operator, and means for requesting operator confirmation of the adapted instructions.

2. The system of claim 1 wherein:
   the controlling means is on line with the infusing means.

3. The system of claim 1 further including:
   means for transferring first signals representative of the sensed physiological conditions to the controlling means and second signals representative of the adapted instructions to the infusing means,
   the signal transferring means further including a first modem locally associated with the infusing means and a second modem locally associated with the controlling means.

4. The system of claim 1 wherein:
   the initial instructions include infusing a first fluid at a first rate of flow and infusing a second fluid at a second rate of flow; and
   the adapted instructions include decreasing the first rate of flow of the first fluid and increasing the second rate of flow of the second fluid.

5. The system of claim 1 wherein:
   the initial instructions include infusing a first fluid; and
   the adapted instructions include stopping the infusing of the first fluid and infusing a second fluid.

6. The system of claim 1 wherein:
   the sensed physiological conditions include at least one of blood pressure, blood sugar level, pulse, respiration rate, and temperature.

7. A system for infusing fluids into a patient comprising:
   a patient infusion system comprising an infusion pump for infusing fluids into a patient in accordance with instructions to carry out a desired course of infusion therapy, a controller for generating initial instructions to carry out a desired course of infusion therapy, said controller in communication with said infusion pump to provide said initial instructions to said pump;
   a physiological sensor for sensing physiological conditions of the patient during the course of infusion;
   a remote infusion controlling system in communication with said patient infusion system and said physiological sensor and located remotely from said patient infusion system comprising:
   memory comprising a data base of condition-result determinations; and
   a controller comprising preprogrammed instructions to monitor the course of infusion and sensed physiological data of the patient and to generate suggested adapted instructions to carry out an adapted course of infusion therapy according to a comparison of the sensed physiological data of the patient to the condition-result determinations; and
   a first modem locally associated with said patient infusion system and a second modem locally associated with said remote infusion controlling system, said first modem and said second modem in communication over a multiple user network.

8. The system of claim 7 wherein:
   the sensed physiological conditions include at least one of blood pressure, blood sugar level, pulse, respiration rate, and temperature.

9. A system for infusing fluids into a patient comprising:
   a patient infusion system comprising an infusion pump for infusing fluids into a patient in accordance with instructions to carry out a desired course of infusion therapy, a controller for generating initial instructions to carry out a desired course of infusion therapy, said controller in communication with said infusion pump to provide said initial instructions to said pump;

a physiological sensor for sensing physiological conditions of the patient during the course of infusion;

a remote infusion controlling system in communication with said patient infusion system and said physiological sensor and located remotely from said patient infusion system comprising:
   memory comprising a data base of condition-result determinations; and
   a controller comprising preprogrammed instructions to monitor the course of infusion and sensed physiological data of the patient and to generate suggested adapted instructions to carry out an adapted course of infusion therapy according to a comparison of the sensed physiological data of the patient to the condition-result determinations;

said initial instructions including infusing a first fluid at a first rate of flow and infusing a second fluid at a second rate of flow; and said suggested adapted instructions including decreasing the first rate of flow of the first fluid and increasing the second rate of flow of the second fluid.

10. A system for infusing fluids into a patient comprising:

a patient infusion system comprising an infusion pump for infusing fluids into a patient in accordance with instructions to carry out a desired course of infusion therapy, a controller for generating initial instructions to carry out a desired course of infusion therapy, said controller in communication with said infusion pump to provide said initial instructions to said pump;

a physiological sensor for sensing physiological conditions of the patient during the course of infusion;

a remote infusion controlling system in communication with said patient infusion system and said physiological sensor and located remotely from said patient infusion system comprising:
   memory comprising a data base of condition-result determinations; and
   a controller comprising preprogrammed instructions to monitor the course of infusion and sensed physiological data of the patient and to generate suggested adapted instructions to carry out an adapted course of infusion therapy according to a comparison of the sensed physiological data of the patient to the condition-result determinations;

said initial instructions including infusing a first fluid; and said adapted instructions including stopping the infusing of the first fluid and infusing a second fluid.

11. A system for infusing fluids into a patient comprising:

a patient infusion system comprising an infusion pump for infusing fluids into a patient in accordance with instructions to carry out a desired course of infusion therapy, a controller for generating initial instructions to carry out a desired course of infusion therapy, said controller in communication with said infusion pump to provide said initial instructions to said pump;

a physiological sensor for sensing physiological conditions of the patient during the course of infusion;

a remote infusion controlling system in communication with said patient infusion system and said physiological sensor and located remotely from said patient infusion system comprising:
   memory comprising a data base of condition-result determinations; and
   a controller comprising preprogrammed instructions to monitor the course of infusion and sensed physiological data of the patient and to generate suggested adapted instructions to carry out an adapted course of infusion therapy according to a comparison of the sensed physiological data of the patient to the condition-result determinations; and said remote infusion controlling system further comprising an operator viewable display and said controller of said remote system further comprising preprogrammed instructions to display said suggested adapted instructions on said operator viewable display and to request operator confirmation of said suggested adapted instructions.

* * * * *